(12) United States Patent
Shapira et al.

(10) Patent No.: US 7,208,477 B2
(45) Date of Patent: Apr. 24, 2007

(54) TREATMENTS FOR BENIGN TUMORS, CANCERS, NEOPLASIAS, AND/OR OTHER INFLAMMATORY DISORDERS OR DISEASES

(75) Inventors: Nathan Andrew Shapira, Gainesville, FL (US); Mary Catherine Lessig, Seattle, WA (US); Bonnie I. McLaurin, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 381 days.

(21) Appl. No.: 10/726,327

(22) Filed: Dec. 1, 2003

(65) Prior Publication Data

US 2004/0191310 A1 Sep. 30, 2004

Related U.S. Application Data

(60) Provisional application No. 60/430,634, filed on Dec. 2, 2002.

(51) Int. Cl.
 *A61K 31/70* (2006.01)
 *A61K 31/35* (2006.01)
(52) U.S. Cl. .................................. 514/27; 514/454
(58) Field of Classification Search .............. 514/23, 514/459, 517, 456, 439
 See application file for complete search history.

(56) References Cited

U.S. PATENT DOCUMENTS

| 4,513,006 | A | * | 4/1985 | Maryanoff et al. ............ 514/23 |
| 5,498,629 | A | * | 3/1996 | Costenzo et al. ............ 514/439 |
| 5,654,461 | A | * | 8/1997 | Choi et al. ..................... 558/48 |
| 5,892,088 | A | * | 4/1999 | Choi et al. ..................... 558/48 |
| 6,071,537 | A | * | 6/2000 | Shank ......................... 424/464 |
| 6,406,716 | B2 | * | 6/2002 | Caruso et al. ............... 424/468 |
| 6,797,692 | B1 | * | 9/2004 | Ikonomidou .................. 514/2 |

FOREIGN PATENT DOCUMENTS

| WO | WO 02/03984 A2 | 1/2002 |
| WO | WO 02/43731 A2 | 6/2002 |
| WO | WO 03/041697 A1 | 5/2003 |

OTHER PUBLICATIONS

B. Ma et a., "Inhibitory effect of topiramate on Lewis lung carcinoma metastasis and its relation with AQP1 water channel", Acta Pharmcol. Sin. vol. 1. pp. 54-60 (Jan. 2004).*
Goldman et al., Cecil Textbook of Medicine. 21st Edition(2000) pp. 1060-1074.*
Morello, F. et al. "Epilepsy and lipoma of hte corpus callosum : 2 cases" Bollettino—*Lega Italiana Contro L'Epilessia 1993 Italy*, No. 82-83, 1993, pp. 237-239.
Relling, Mary V., et al. "Adverse effect on anticonvulsants on efficacy of chemotherapy for acute lymphoblastic leukaemia" *Lancet* (North American Edition), 356(9226):285-290, 2000.

* cited by examiner

*Primary Examiner*—Raymond J Henley, III
(74) *Attorney, Agent, or Firm*—Saliwanchik, Lloyd & Saliwanchik

(57) ABSTRACT

The subject invention provides methods and compositions for the treatment of benign tumors, cancers, neoplasias, and/or other inflammatory disorders or diseases. In the practice of the subject invention, and anti-convulsant agent, such as topiramate, is administered to an individual.

5 Claims, 1 Drawing Sheet
(1 of 1 Drawing Sheet(s) Filed in Color)

TREATMENTS FOR BENIGN TUMORS, CANCERS, NEOPLASIAS, AND/OR OTHER INFLAMMATORY DISORDERS OR DISEASES

CROSS-REFERENCE TO RELATED APPLICATION(S)

This application is claims the benefit of U.S. Provisional Application No. 60/430,634, filed Dec. 2, 2002, which is hereby incorporated by reference in its entirety, including all figures, tables, and drawings.

BRIEF SUMMARY OF THE INVENTION

The subject invention provides methods and compositions for the treatment of benign tumors, cancers, neoplasias, and/or other inflammatory disorders or diseases. In the practice of the subject invention, an anti-convulsant agent, such as topiramate, is administered to an individual, optionally, with additional therapeutic agents for the treatment of the aforementioned conditions.

Exemplary benign tumors that can be treated according to the subject invention include, and are not limited to, hemangiomas such as cavernous hemangioma, hepatocellular adenoma, cavernous hemangioma, focal nodular hyperplasia, acoustic neuromas, neurofibroma, bile duct adenoma, bile duct cystanoma, fibroma, lipomas, benign bone tumors, leiomyomas, mesotheliomas, teratomas, myxomas, nodular regenerative hyperplasia, trachomas and granulomatous inflammatory diseases both infectious, such as pyogenic granulomas, and non-infectious or idiopathic, such as sarcoidosis and berylliosis.

Specific types of cancers or neoplasias, both primary and secondary, that can be treated in accordance with this this invention include both carcinomas and sarcomas. Non-limiting examples of specific carcinomas and sarcomas include leukemia, breast cancer, skin cancer, bone cancer, prostate cancer, liver cancer, lung cancer, neurological tumors of the brain, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian cancer, leiomyomas, cervical dysplasia and other in situ carcinomas, neuroblastoma, retinoblastoma, soft tissue sarcoma, malignant carcinoid, topical skin lesion, mycosis flngoides, rhabdomyosarcoma, Kaposi's sarcoma, osteogenic and other sarcomas, malignant hypercalcemia, renal cell tumor, polycythemia vera, adenocarcinomas, glioblastoma multiform a, leukemias, lymphomas, melanoma, and epidermoid carcinomas.

The subject invention can also be used to treat a variety of inflammatory disorders or diseases including, but not limited to, inflammatory bowel disease, mumps (e.g., myxo virus infections), meningitis, encephalitis, inflammation of the larynx (e.g., laryngotracheitis (croup); supraglottitis (epiglottitis); diphtheria; spasmodic croup, traumatic laryngitis; common upper respiratory infection; laryngotracheitis supraglottitis; laryngeal abscess), chronic (granulomatous) diseases such as tuberculosis, leprosy, scleroma, actinomycosis, tularemia, glanders, spirochetal (syphilis), candidiasis blastomycosis, histoplasmosis, coccidiomycosis, aspergillosis, sarcoidosis, Wegener's granulomatosis, angioedema, Stevens-Johnson syndrome, rheumatoid arthritis, systemic lupus erythematosus, cicatricial pemphigoid, relapsing polychondritis, Sjogren's syndrome, amyloidosis, trichinosis, leishmaniasis, schistosomiasis, syngamus laryngeus, inhalation laryngitis (e.g., acute (thermal) injury, pollution and inhalant allergy, and carcinogens), radiation injury (e.g., radiation laryngitis or radionecrosis) and vocal abuse and misuse syndromes (such as vocal-cord hemorrhage, muscle tension dysphonias, and contact ulcer and granuloma).

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

DETAILED DISCLOSURE OF THE INVENTION

Figure 1A:
FIG. 1A, depicts the size of a lipoma on a dog treated with topiramate for 24 days.

The subject invention provides methods and compositions for the treatment of benign tumors, cancers, neoplasias, and/or other inflammatory disorders or diseases. In the practice of the subject invention, topiramate is administered to an individual in amounts sufficient to mediate a therapeutic effect in the individual. In a preferred embodiment, the administration of topiramate decreases inflammation (or swelling) associated with a particular disease or disorder. For example, inflammation is associated with a variety of diseases such as benign tumors, malignant tumors, cancers, or neoplasias, viral infections, bacterial infections, or fungal infections. Thus, the subject invention provides a method of treating inflammation or swelling associated with a disease or disorder comprising the administration of topiramate in amounts sufficient to reduce or eliminate the disease or disorder associated swelling.

In accordance with the instant invention, topiramate can be administered alone to the individual or in combination with other therapeutic agents or modalities used to treat a particular disease or disorder. For example, topiramate can be used with any conventional chemotherapeutic agent(s) used in the treatment of benign or malignant tumors, cancers, or neoplasias, radiation treatment, or surgical intervention (e.g., tumor resection). Thus, it is also an aspect of this invention that anti-convulsant compositions described herein, can be combined with other chemotherapeutic agents for the treatment of the diseases and disorders discussed above. For instance, an anti-convulsant formulation according to the invention can be combined with alkylating agents such as fluorouracil (5-FU) alone or in further combination with leukovorin; or other alkylating agents such as, without limitation, other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethio-phosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma). Likewise the formulation of the invention can be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. The formulation according to the present invention can also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposils sarcoma; the antibiotic chemotherapeutic agents, e.g., daunorubicin, doxorubicin, epirubicin, idarubicin, and mitomycin (used to treat stomach, cervix, colon, breast, bladder and pancreatic cancer), dactinomycin, temozolomide, plicamycin, bleomycin (used in the treatment of skin, esophagus and genitourinary tract cancer); nemorubicin and the enzymatic chemotherapeutic agents such as L-asparaginase. In addition to the above, the formulation of the present invention can be expected to have a beneficial effect used in combination with other platinum coordination complexes, e.g., cisplatin and carboplatin; substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as, e.g., formestane, fadrozole, letrozole, anastrozole and exemestane). In other embodiments, anticonvulsant compositions of the subject invention can further comprise therapeutic agents such as anti-fungal agents, anti-viral agents, or antibiotics typically used to treat fungal, viral, or bacterial infections.

Exemplary benign tumors that can be treated according to the subject invention include, and are not limited to, hemangiomas such as cavernous hemangioma, hepatocellular adenoma, cavernous hemangioma, focal nodular hyperplasia, acoustic neuromas, neurofibroma, bile duct adenoma, bile duct cystanoma, fibroma, lipomas, benign bone tumors, leiomyomas, mesotheliomas, teratomas, myxomas, nodular regenerative hyperplasia, trachomas and granulomatous inflammatory diseases both infectious, such as pyogenic granulomas, and non-infectious or idiopathic, such as sarcoidosis and berylliosis.

Specific types of malignant cancers, tumors, or neoplasias that can be treated in accordance with this invention include both carcinomas and sarcomas. Non-limiting examples of specific carcinomas and sarcomas include leukemia, breast cancer, skin cancer, bone cancer, prostate cancer, liver cancer, lung cancer, neurological tumors of the brain, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian cancer, leiomyomas, cervical dysplasia and other in situ carcinomas, neuroblastoma, retinoblastoma, soft tissue sarcoma, malignant carcinoid, topical skin lesion, mycosis fungoides, rhabdomyosarcoma, Kaposi's sarcoma, osteogenic and other sarcomas, malignant hypercalcemia, renal cell tumor, polycythemia vera, adenocarcinomas, glioblastoma multiform a, leukemias, lymphomas, melanoma, and epidermoid carcinomas.

The subject invention can also be used to treat a variety of inflammatory disorders or diseases including, but not limited to, inflammatory bowel disease, mumps (e.g., myxo virus infections), meningitis, encephalitis, inflammation of the larynx (e.g., laryngotracheitis (croup); supraglottitis (epiglottitis); diphtheria; spasmodic croup, traumatic laryngitis; common upper respiratory infection; laryngotracheitis supraglottitis; laryngeal abscess), chronic (granulomatous) diseases such as tuberculosis, leprosy, scleroma, actinomycosis, tularemia, glanders, spirochetal (syphilis), candidiasis blastomycosis, histoplasmosis, coccidiomycosis, aspergillosis, sarcoidosis, Wegener's granulomatosis, angioedema, Stevens-Johnson syndrome, rheumatoid arthritis, systemic lupus erythematosus, cicatricial pemphigoid, relapsing polychondritis, Sjogren's syndrome, amyloidosis, trichinosis, leishmaniasis, schistosomiasis, syngamus laryngeus, inhalation laryngitis (e.g., acute (thermal) injury, pollution and inhalant allergy, and carcinogens), radiation injury (e.g., radiation laryngitis or radionecrosis) and vocal abuse and misuse syndromes (such as vocal-cord hemorrhage, muscle tension dysphonias, and contact ulcer and granuloma).

The subject invention provides methods having both human and veterinary utility. The term "individual" includes animals of avian, mammalian, or reptilian origin. Mammalian species which benefit from the disclosed methods include, and are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, duckbill platypus, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans.

Compounds of formulas I–V are anti-epileptic compounds, which are highly effective anti-convulsants. The compounds useful in the practice of the instant invention include the individual isomers, analogs, and homologs of the disclosed anti-convulsant compounds. Racemic mixtures, as well as the isolated enantiomeric forms, of the compounds can also be used in the practice of the subject invention.

In addition, the compounds useful for the practice of the subject invention include pharmaceutically acceptable salts, for example; alkali metal salts, such as sodium or potassium, ammonium salts, dialkyammonium salts, trialkylammonium salts, tetraalkylammonium salts, and tromethamine salts. Hydrates and other solvates of the compounds are also included within the scope of the compounds useful in the practice of this invention.

One such compound is taught and disclosed in U.S. Pat. No. 4,513,006, hereby incorporated by reference in its entirety. 2,3:4,5-bis-O-(1-methylethylidene)-β-D-fructopyranose sulfamate, known as topiramate, has been demonstrated in clinical trials of human epilepsy to be effective as adjunctive therapy or as monotherapy in treating simple and complex partial seizures and secondarily generalized seizures. Other useful compounds include those described by formula I, including (tetrahydro-2H-pyran-2-yl)methane sulfamate, and 2,3:4,5-bis-O-(1-methylethylidene)-β-D-fructopyranose methylsulfamate

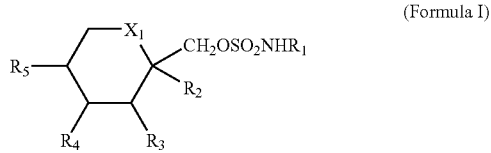

(Formula I)

wherein $X_1$ is $CH_2$ or oxygen;

$R_1$ is hydrogen or alkyl; and $R_2$, $R_3$, $R_4$, and $R_5$ are independently hydrogen or lower alkyl and, when $X_1$ is $CH_2$, $R_4$, and $R_5$ may be alkene groups joined to form a benzene ring and, when $X_1$ is oxygen, $R_2$ and $R_3$ and/or $R_4$ and $R_5$ together may be a methylenedioxy group of the following formula:

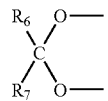

wherein $R_6$ and $R_7$ are the same or different and are hydrogen, lower alkyl or are alkyl and are joined to form a cyclopentyl or cyclohexyl ring.

For compounds of formula I, $R_1$ may be hydrogen or an alkyl of about 1 to 4 carbons, such as methyl, ethyl, and isopropyl. Alkyl includes straight and branched chain alkyl. For compounds of formula I, Alkyl groups for $R_2$, $R_3$, $R_4$, $R_5$, $R_6$, and $R_7$ are of about 1 to 3 carbons and include methyl, ethyl, isopropyl and N-propyl.

When $X_1$ is $CH_2$, $R_4$ and $R_5$ may combine to form a benzene ring fused to the 6-membered $X_1$-containing ring, i.e., $R_4$ and $R_5$ are defined by the alkatrienyl group =CH—CH=CH—CH=.

In one embodiment, $X_1$ is oxygen and both $R_2$ and $R_3$ and $R_4$ and $R_5$ together are methylenedioxy groups of the formula wherein $R_6$ and $R_7$ are both hydrogen, both alkyl or combine to form a spiro cyclopentyl or cyclohexyl ring, in particularly where $R_6$ and $R_7$ are both alkyl such as methyl.

In another embodiment, $X_1$ is $CH_2$ and $R_4$ and $R_5$ are joined to form a benzene ring. Another embodiment provides compounds of formula (I) wherein both $R_2$ and $R_3$ are hydrogen.

Other compounds (formulas II–VI) and compositions useful in the practice of the subject invention may be found in the teachings of U.S. Pat. Nos. 5,384,327, 5,498,629, 5,654,461, 5,892,088, and 6,071,537, each of which is incorporated by reference in their entireties.

These compounds include those provided by the structure:

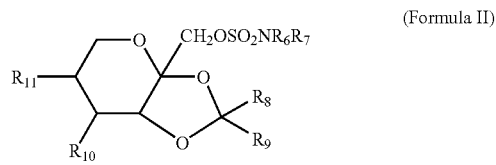

(Formula II)

wherein $R_6$ and $R_7$ may be the same or different and are selected from any of hydrogen or $C_1$ to $C_4$ alkyl. In one embodiment, $R_6$ and $R_7$ are each hydrogen.

$R_8$ and $R_9$ may be the same or different and are selected from any of hydrogen or $C_1$ to $C_4$ alkyl. In one embodiment, $R_8$ and $R_9$ are each $C_1$ to $C_4$ alkyl.

$R_{10}$ and $R_{11}$ may be the same or different and are selected from any of azido, halogen, hydroxyl, sulfamoyl ($H_2NSO_2O$), $C_1$ to $C_4$ alkoxy, $C_1$ to $C_4$ alkyl thiocarbonate (RSC(O)O), $C_1$ to $C_4$ alkyl carbonate (ROC(O)O), or $C_1$ to $C_4$ alkyl carboxylate (RC(O)O), wherein R is $C_1$ to $C_4$ alkyl. In one embodiment, $R_{10}$ and $R_{11}$ are selected from any of $C_1$–$C_4$ alkyl thiocarbonate, halogen or hydroxyl.

For compounds of formula II, the terms alkyl and alkoxy include straight and branched chains. For example, alkyl radicals include methyl, ethyl, propyl, isopropyl, n-butyl, isobutyl, and t-butyl. Halogen includes bromine, chlorine, fluoride and iodine.

Preferred compounds of the formula (II) are those wherein the pyran ring is in the L-sorbopyranose absolute configuration. Particularly preferred compounds of formula (II) are those wherein the pyran ring is in the L-sorbopyranose absolute configuration, $R_6$ and $R_7$ are each hydrogen, $R_8$ and $R_9$ are each methyl; $R_{10}$ is methyl thiocarbonate ($CH_3SC(O)O$) and $R_{11}$ is halogen; or $R_{10}$ and $R_{11}$ are both halogen; or $R_{10}$ is hydroxyl and $R_{11}$ is halogen. Particularly preferred halogens include bromine, chlorine, and iodine.

Specific examples of compounds of formula (II) are: (1) 5-deoxy-5-iodo-2,3-O-(1-methylethylidene)-4-[methylthiocarbonyl)]-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ is $CH_3SC(O)O$, and $R_{11}$ is iodine); (2) 4,5-dibromo-4,5-dideoxy-2,3-O-(1-methylethylidene)-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ and $R_{11}$ are bromine); and (3) 5-chloro-5-deoxy-2,3-O-(1-methylethylidene)-α-L-sorbopyranose sulfamate, (i.e., where the compound is in the L-sorbopyranose absolute configuration, $R_6$ and $R_7$ are hydrogen, $R_8$ and $R_9$ are methyl, $R_{10}$ is hydroxyl, and $R_{11}$ is chlorine).

Another compound useful in the practice of the invention is described in Formula III:

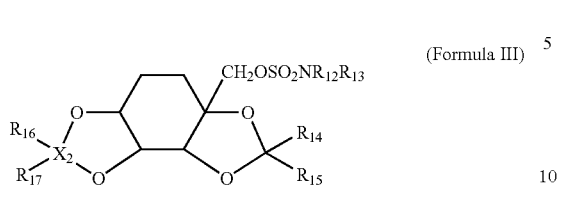

(Formula III)

wherein $R_{12}$ and $R_{13}$ are the same or different and are selected from any of hydrogen, alkyl ($C_1$ to $C_6$), cycloalkyl ($C_3$–$C_7$), allyl, or benzyl. In one embodiment, $R_{12}$ and $R_{13}$ are each hydrogen. $R_{14}$ and $R_{15}$ are the same or different and selected from hydrogen or lower alkyl.

$X_2$ may be chosen from carbon (C) or sulfur (S), with the stipulation that when $X_2$ is carbon, $R_{16}$ and $R_{17}$ are the same or different and are selected from hydrogen or lower alkyl, whereas when $X_2$ is sulfur one of $R_{16}$ and $R_{17}$ is oxygen and the other is a lone pair of electrons or both $R_{16}$ and $R_{17}$ are oxygen.

For compounds of formula III, the term alkyl includes straight and branched chains. For example, alkyl radicals include methyl, ethyl, propyl, isopropyl, n-butyl, isobutyl, and t-butyl.

Particularly preferred compounds of formula III are: (1) (1R,2R,3S,4S)-(1,2:3,4-di-O-methylethylidenecyclohexan-1,2,3,4-tetraol-r-yl)methyl sulfamate, (i.e., where $R_{12}$ and $R_{13}$ are hydrogen, $R_{14}$, $R_{15}$, $R_{16}$, and $R_{17}$ are methyl and $X_2$ is carbon); (2) (1R,2S,3S,4S)-(3,4-O-methylethylidene-1,2-O-sulfonyl-cyclohexan-1,2,3,4-tetraol-4-yl)methyl sulfamate, (i.e., where $R_{12}$ and $R_{13}$ are hydrogen, $R_{14}$ and $R_{15}$ are methyl, $R_{16}$ is oxygen and $R_{17}$ is an electron pair and $X_2$ is sulfur); and (3) (1R,2S,3S,4S)-(3,4-O-methylethylidene-1,2-O-sulfonyl-cyclohexan-1,2,3,4-tetraol-4-yl)methyl sulfamate, (i.e., where $R_{12}$ and $R_{13}$ are hydrogen, $R_{14}$ and $R_{15}$ are methyl, $R_{16}$ and $R_{17}$ are both oxygen and $X_2$ is sulfur).

Another compound useful in the subject invention is

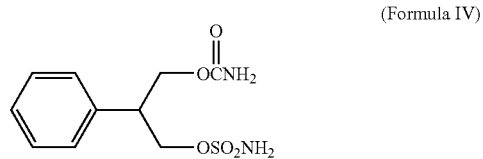

(Formula IV)

Other compounds useful in the practice of the invention include those of Formula V

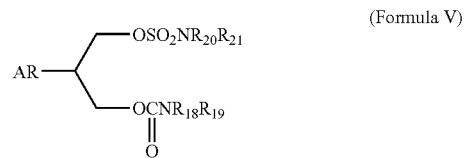

(Formula V)

wherein, AR is represented by the following formulas:

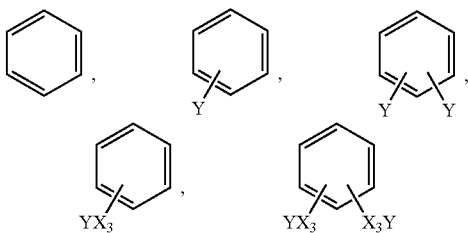

Y is selected from the group consisting of halogens such as F, Cl, Br and I, or trifluoromethyl and alkyl groups containing 1 to 3 carbon atoms when Y alone is attached to the benzene ring; when $X_3$, which may be S or O, is present, Y is selected from the group consisting of trifluoromethyl and alkyl groups containing 1 to 3 carbon atoms. $R_{18}$, $R_{19}$, $R_{20}$, and $R_{21}$, may be identical or different and are selected from the group consisting of hydrogen, linear or branched alkyl groups containing 1 to 16 carbon atoms, cyclic alkyl groups containing 3 to 16 carbon atoms and aryl groups containing 6 to 8 carbon atoms, and $NR_{18}R_{19}$ and $NR_{20}R_{21}$, identical or different, each may form a 3 to 7-membered aliphatic cyclic compound together with another nitrogen atom or oxygen atom.

Compositions useful in the practice of this invention comprise one or more of the compounds of formulas I–V admixed with a pharmaceutical carrier and, optionally, additional therapeutic agents as set forth above. The compositions may be made according to conventional pharmaceutical compounding techniques. Thus, the carrier may take a wide variety of forms depending on the form of preparation desired for administration, e.g., injection, oral, suppository, topical, or parenteral. In some embodiments, the composition can further comprise additional therapeutic agents used to treat a particular disease, disorder, benign tumor, or malignancy.

In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like.

Because of their ease in administration, tablets and capsules represent the most advantageous oral dosage unit form, in which case solid pharmaceutical carriers are employed. If desired, tablets may be sugar coated or enteric coated by standard techniques. Suppositories may be prepared, in which case cocoa butter could be used as the carrier.

For parenterals, the carrier will usually comprise sterile water, though other ingredients, for example, for purposes such as aiding solubility or for preservation, may be included. Injectable suspensions may also be prepared in which case appropriate liquid carriers, suspending agents and the like may be employed.

Other compositions useful in the practice of the subject invention include salves, cosmetics, ointments, and the like. Such compositions may be topically applied to a site or incorporated into articles of manufacture including, but not limited to, bandages, adhesive strips for the covering of wounds (e.g., BANDAID brand adhesive strips), or transdermal patches. Carriers such as cocoa butter, viscous polyethylene glycols, hydrogenated oils, and such mixtures can be emulsified if desired.

Compounds of the subject invention may also be incorporated into cosmetics. Additional materials and substances suitable as carriers for the compounds of formulas I–V are described in the International Cosmetic Ingredient Dictionary and Handbook, $8^{th}$ Edition (The Cosmetic, Toiletry, and Fragrance Association (CTFA), 2000), hereby incorporated by reference in its entirety.

Where the pharmaceutical compositions are aerosols, the active ingredients can be packaged in pressurized aerosol containers with a propellant, e.g., carbon dioxide, nitrogen, propane, etc. with the usual adjuvants such as cosolvents, wetting agents, etc.

In accordance with the invention, pharmaceutical compositions comprise, as an inactive ingredient, an effective amount of one or more non-toxic, pharmaceutically acceptable ingredient(s). Examples of such ingredients for use in the compositions include ethanol, dimethyl sulfoxide, glycerol, silica, alumina, starch, calcium carbonate, talc, flour, and equivalent non-toxic carriers and diluents.

The pharmaceutical compositions described herein will contain, per dosage unit, e.g., tablet, capsule, powder injection, teaspoonful, suppository, bandage, and the like, from about 0.1 to about 2000 mg; about 100 to about 1900 mg; about 200 to about 1800 mg; about 300 to about 1700 mg; about 400 to about 1600 mg; about 500 to about 1500 mg; about 600 to about 1400 mg; about 700 to about 1300 mg; or about 800 to about 1200 mg of the active ingredient (anti-convulsant agents, such as the compounds of Formulae I–V). In a preferred embodiment, the compositions comprise about 10 mg to 400 mg, or more preferably about 10 mg to about 200 mg per dosage unit. In an even more preferred embodiment, the compositions contain comprise about 20 mg to about 100 mg of active ingredient. In another embodiment, the compositions comprise about 25 mg of active ingredient per unit dose.

Topiramate is currently available for oral administration in round tablets containing 25 mg, 100 mg or 200 mg of active agent. The tablets contain the following inactive ingredients: lactose hydrous, pregelatinized starch, microcrystalline cellulose, sodium starch glycolate, magnesium stearate, purified water, carnauba wax, hydroxypropyl methyl cellulose, titanium dioxide, polyethylene glycol, synthetic iron oxide, and polysorbate 80.

Thus, as illustrated herein, the subject invention provides the following non-limiting embodiments:

1. A method for treating or controlling or reducing swelling (or inflammation) associated with a disease, disorder, benign tumor, malignant tumor, malignant cancer, or malignant neoplasia in an individual comprising the administration of a therapeutically effective amount of a composition comprising an anti-convulsant agent and a pharmaceutically acceptable carrier;

2. The method according to embodiment 1, wherein the composition further comprises one or more additional therapeutic agent for the treatment of a disease, disorder, benign tumor, malignant tumor, malignant cancer, or malignant neoplasias;

3. The method according to embodiments 1 or 2, wherein the disease, disorder, benign tumor, malignant tumor, malignant cancer, or malignant neoplasia is selected from the group consisting of hemangiomas such as cavernous hemangioma, hepatocellular adenoma, cavernous hemangioma, focal nodular hyperplasia, acoustic neuromas, neurofibroma, bile duct adenoma, bile duct cystanoma, fibroma, lipomas, benign bone tumors, leiomyomas, mesotheliomas, teratomas, myxomas, nodular regenerative hyperplasia, trachomas and granulomatous inflammatory diseases both infectious, such as pyogenic granulomas, sarcoidosis, berylliosis, leukemia, breast cancer, skin cancer, bone cancer, prostate cancer, liver cancer, lung cancer, neurological tumors of the brain, cancer of the larynx, gallbladder, pancreas, rectum, parathyroid, thyroid, adrenal, neural tissue, head and neck, colon, stomach, bronchi, kidneys, basal cell carcinoma, squamous cell carcinoma of both ulcerating and papillary type, metastatic skin carcinoma, osteosarcoma, Ewing's sarcoma, reticulum cell sarcoma, myeloma, giant cell tumor, small-cell lung tumor, gallstones, islet cell tumor, primary brain tumor, acute and chronic lymphocytic and granulocytic tumors, hairy-cell tumor, adenoma, hyperplasia, medullary carcinoma, pheochromocytoma, mucosal neuromas, intestinal ganglioneuromas, hyperplastic corneal nerve tumor, marfanoid habitus tumor, Wilm's tumor, seminoma, ovarian cancer, leiomyomas, cervical dysplasia and other in situ carcinomas, neuroblastoma, retinoblastoma, soft tissue sarcoma, malignant carcinoid, topical skin lesion, mycosis fuingoides, rhabdomyosarcoma, Kaposi's sarcoma, osteogenic and other sarcomas, malignant hypercalcemia, renal cell tumor, polycythemia vera, adenocarcinomas, astrocytomas, glioblastoma multiform a, leukemias, lymphomas, melanoma, epidermoid carcinomas, inflammatory disorders or diseases including, but not limited to, inflammatory bowel disease, mumps (e.g., myxo virus infections), meningitis, encephalitis, inflammation of the larynx (e.g., laryngotracheitis (croup); supraglottitis (epiglottitis); diphtheria; spasmodic croup, traumatic laryngitis; common upper respiratory infection; laryngotracheitis supraglottitis; laryngeal abscess), chronic (granulomatous) diseases such as tuberculosis, leprosy, scleroma, actinomycosis, tularemia, glanders, spirochetal (syphilis), candidiasis blastomycosis, histoplasmosis, coccidiomycosis, aspergillosis, sarcoidosis, Wegener's granulomatosis, angioedema, Stevens-Johnson syndrome, rheumatoid arthritis, systemic lupus erythematosus, cicatricial pemphigoid, relapsing polychondritis, Sjogren's syndrome, amyloidosis, trichinosis, leishmaniasis, schistosomiasis, syngamus laryngeus, inhalation laryngitis (e.g., acute (thermal) injury, pollution and inhalant allergy, and carcinogens), radiation injury (e.g., radiation laryngitis or radionecrosis), vocal abuse and misuse syndromes (such as vocal-cord hemorrhage, muscle tension dysphonias, and contact ulcer and granuloma); and 4. The method according to any preceding embodiment, wherein the "individual" includes animals of avian, mammalian, or reptilian origin. Mammalian species which benefit from the disclosed methods include, and are not limited to, apes, chimpanzees, orangutans, humans, monkeys; domesticated animals (pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, duckbill platypus, kangaroo, opossums, raccoons, pandas, giant pandas, hyena, seals, sea lions, and elephant seals. Reptiles include, and are not limited to, alligators, crocodiles, turtles, tortoises, snakes, iguanas, and/or other lizards. Avian species include, and are not limited to, chickens, turkeys, pigeons, quail, parrots, macaws, dove, Guinea hens, lovebirds, parakeets, flamingos, eagles, hawks, falcons, condor, ostriches, peacocks, ducks, and swans; and 5. The method according to any preceding embodiment, wherein the anti-convulsant agent is one or more compound as set forth in Formulae I, II, III, IV, or V (or individual isomers, analogs, homologs of the compounds of Formulae I, II, II, IV, or V and/or combinations of individual isomers, analogs, homologs of the compounds of Formulae I, II, IfI, IV, or V) and can be administered alone to the individual or in combination with other therapeutic agents or modalities used to treat a particular disease or disorder (e.g., the compositions comprise one or more compound as set forth in Formulae I, II, III, IV, or V (or individual isomers, analogs, homologs of the compounds of Formulae I, II, III, IV, or V and/or combinations of individual isomers, analogs, homologs of the compounds of Formulae I, II, III, IV, or V) and, optionally, a therapeutic agent). For example, topiramate can be used with any conventional chemotherapeutic agent(s) used in the treatment of benign or malignant tumors, cancers, or neoplasias, radiation treatment, or surgical intervention (e.g., tumor resection). Thus, it is also an aspect of this invention that anti-convulsant compositions described herein, can be combined with other chemotherapeutic agents for the treatment of the diseases and disorders discussed above. For instance, an anti-convulsant formulation according to the invention can be combined with alkylating agents such as fluorouracil (5-FU) alone or in further combination with leukovorin; or other alkylating agents such as, without limitation, other pyrimidine analogs such as UFT, capecitabine, gemcitabine and cytarabine; the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethio-phosphoramide and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembrichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma). Likewise the formulation of the invention can be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungiodes breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias. The formulation according to the present invention can also be expected to prove efficacious in combination with natural product based chemotherapeutic agents such as, without limitation, the vinca alkaloids, e.g., vinblastin (used in the treatment of breast and testicular cancer), vincristine and vindesine; the epipodophylotoxins, e.g., etoposide and teniposide, both of which are useful in the treatment of testicular cancer and Kaposils sarcoma; the antibiotic chemotherapeutic agents, e.g., daunorubicin, doxorubicin, epirubicin, idarubicin, and mitomycin (used to treat stomach, cervix, colon, breast, bladder and pancreatic cancer), dactinomycin, temozolomide, plicamycin, bleomycin (used in the treatment of skin, esophagus and genitourinary tract cancer); nemorubicin and the enzymatic chemotherapeutic agents such as L-asparaginase. In addition to the above, the formulation of the present invention can be expected to have a beneficial effect used in combination with other platinum coordination complexes, e.g., cisplatin and carboplatin; substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbesterol); antiestrogens such as tamoxifen; androgens, e.g., testosterone propionate; and aromatase inhibitors (such as, e.g., formestane, fadrozole, letrozole, anastrozole and exemestane). In other embodiments, anti-convulsant compositions of the subject invention can further comprise anti-fungal agents, anti-viral agents, or antibiotics typically used to treat fungal, viral, or bacterial infections.

It should be understood that the examples and embodiments described herein are for illustrative purposes only and that various modifications or changes in light thereof will be suggested to persons skilled in the art and are to be included within the spirit and purview of this application and the scope of the appended embodiments. All publications and patents cited herein are hereby incorporated by reference in their entireties.

EXAMPLE 1

Effects of Toriramate on Lipoma

Figure 1B:
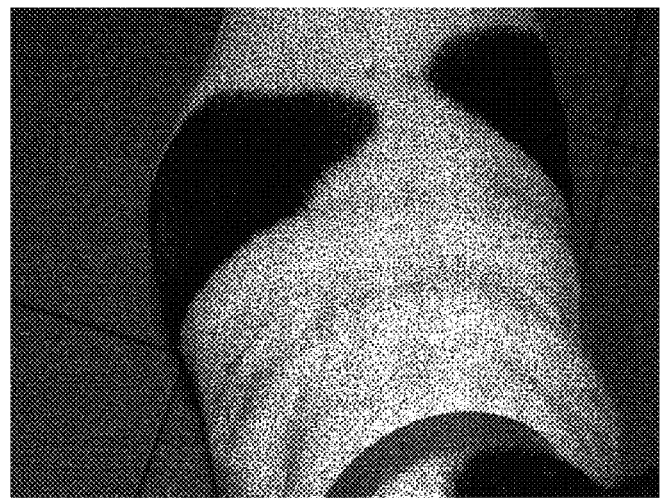
FIG. 1B illustrates the reduction in lipoma size on the dog after topiramate had been administered for 59 days (25 mg/day administered once per day). The lipoma had shrunk considerably while the animal was on topiramate

A 12-year-old female neutered German Shorthaired Pointer (30.8 kg) has had a large lipoma for 6 years duration on the right rib cage of the animal. FIG. 1A shows the dog (on 25 mg a day of topiramate) after 24 days. FIG. 1B illustrates the reduction in lipoma mass on the dog after topiramate had been administered for 59 days (25 mg/day administered once per day) The lipoma had shrunk considerably while the animal was on topiramate.

We claim:

1. A method for treating lipomas or controlling lipomas or reducing swelling or inflammation associated with lipomas, in an individual comprising the administration of an effective amount of a composition comprising an anti-convulsant agent selected from topiramate or pharmaceutically acceptable salts thereof and a pharmaceutically acceptable carrier to said individual, wherein said effective amount is sufficient to eliminate or treat a lipoma, control a lipoma or reduce swelling or inflammation associated with lipomas.

2. The method according to claim 1, wherein the composition further comprises one or more additional therapeutic agent.

3. The method according to claim 2, wherein said additional therapeutic agent is selected from the group consisting of alkylating agents, antimetabolite chemotherapeutic agents, vinea alkaloids, antibiotic chemotherapeutic agents, enzymatic chemotherapeutic agents, platinum coordination complexes, substituted ureas, adrenocortical suppressants, hormone and hormone antagonists, antiestrogens, androgens aromatase inhibitors, anti-fungal agents, anti-viral agents, or antibiotics.

4. The method according to claim 1, wherein said anti-convulsant is topiramate.

5. The method according to claim 1, wherein said anti-convulsant is a phamaceutically acceptable salt of topiramate.

* * * * *

UNITED STATES PATENT AND TRADEMARK OFFICE
CERTIFICATE OF CORRECTION

PATENT NO. : 7,208,477 B2
APPLICATION NO. : 10/726327
DATED : April 24, 2007
INVENTOR(S) : Nathan Andrew Shapira, Mary Catherine Lessig and Bonnie I. McLaurin It is certified that error appears in the above-identified patent and that said Letters Patent is hereby corrected as shown below:

Column 1,
Line 50, "hyperplastic comeal" should read --hyperplastic corneal--.
Line 55, "mycosis flngoides" should read --mycosis fungoides--.

Column 10,
Line 23, "fuingoides" should read --fungoides--.

Column 12,
Line 47, "to eliminate or treat a lipoma" should read --to treat a lipoma--.
Line 55, "vinea alkaloids" should read --vinca alkaloids--.
Line 64, "phamaceutically acceptable" should read --pharmaceutically acceptable--.

Signed and Sealed this

Fourth Day of September, 2007

JON W. DUDAS
*Director of the United States Patent and Trademark Office*